(12) United States Patent
Lee et al.

(10) Patent No.: US 7,220,229 B2
(45) Date of Patent: May 22, 2007

(54) DENSITY/SOLUTE MONITOR OF MULTI-MODALITIES AND SIGNAL PROCESSING SCHEME

(75) Inventors: Lian-Pin Lee, Charlottesville, VA (US); Jen-Shih Lee, Charlottesville, VA (US); Shyh-Hau Wang, Shin Juang (TW); Mike Min, Earlysville, VA (US)

(73) Assignee: Global Monitors, Inc., Rancho Sante Fe, CA (US)

( * ) Notice: Subject to any disclaimer, the term of this patent is extended or adjusted under 35 U.S.C. 154(b) by 486 days.

(21) Appl. No.: 10/689,450

(22) Filed: Oct. 20, 2003

(65) Prior Publication Data

US 2004/0087860 A1    May 6, 2004

Related U.S. Application Data

(63) Continuation-in-part of application No. 10/274,086, filed on Oct. 18, 2002, now Pat. No. 6,740,036, which is a continuation-in-part of application No. 09/908,223, filed on Jul. 18, 2001, now Pat. No. 6,485,427.

(60) Provisional application No. 60/218,906, filed on Jul. 18, 2000.

(51) Int. Cl.
*A61B 8/00* (2006.01)

(52) U.S. Cl. .................. 600/438; 600/368; 73/1.82

(58) Field of Classification Search ........ 600/437–438, 600/368, 309, 322, 328, 331, 449; 73/1.82; 210/739–740
See application file for complete search history.

(56) References Cited

U.S. PATENT DOCUMENTS

| | | | | |
|---|---|---|---|---|
| 5,935,066 A | * | 8/1999 | Harris | 600/436 |
| 5,959,601 A | * | 9/1999 | Ho et al. | 73/579 |
| 6,390,999 B1 | * | 5/2002 | Zscheile et al. | 604/4.01 |
| 6,413,098 B1 | * | 7/2002 | Tallal et al. | 600/310 |
| 6,485,427 B1 | * | 11/2002 | Lee et al. | 600/468 |
| 6,740,036 B1 | * | 5/2004 | Lee et al. | 600/437 |
| 2002/0101373 A1 | * | 8/2002 | Arndt et al. | 342/124 |

\* cited by examiner

*Primary Examiner*—Francis J. Jaworski
(74) *Attorney, Agent, or Firm*—Jagtiani & Guttag

(57) ABSTRACT

A density/solute monitor having at least one ultrasound probe, a signal processing unit, and a computing mechanism, and process for using the same, to measure phase shift between emitting and receiving ultrasound, sound velocity, compressibility, density, and solute concentration of fluid flowing through a fluid processing system. The ultrasound probe emits and receives ultrasound waves through the fluid and the signal-processing unit and computing mechanism process the ultrasound waves to determine phase and time shift. The computing mechanism converts phase shift to density, compressibility, and solute concentration measurements of the fluid. Calibrating fluids calibrate the detected phase shift in terms of sound velocity in the factory. Measurements provide information about passage of solutes and flow to achieve better solute collection efficiency, solution purity, and control of fluid processing systems. The density/solute monitor can include other detection modalities such as an optical probe, making concentration measurements of the density/solute monitor more specific to selected solutes.

65 Claims, 5 Drawing Sheets

DENSITY/SOLUTE MONITOR OF MULTI-MODALITIES AND SIGNAL PROCESSING SCHEME

This application is a continuation-in-part of Ser. No. 10/274,086, filed Oct. 18, 2002, now U.S. Pat. No. 6,740,036, filed Oct. 18, 2002 and issued on May 25, 2004, which is continuation-in-part of Ser. No. 09/908,223, filed Jul. 18, 2001, now of U.S. Pat. No. 6,485,427 B1, filed Jul. 18, 2001 and issued on Nov. 26, 2002, and U.S. Provisional Application 60/218,906, filed Jul. 18, 2000.

FIELD OF THE INVENTION

This invention generally relates to a device and method for monitoring fluid properties, and specifically relates to a density/solute monitor having ultrasound probes for continuous monitoring of the ultrasound velocity of fluid in a biological or chemical processing system in order to determine fluid density, compressibility, solute concentration, and the fluid flow and a method for using the same wherein the probes are integrated with modality measurements such as optical absorbance, conductivity, impedance, magnetic resonance, radiation attenuation, and tracers of fluid.

BACKGROUND

Two classical methods of measuring density of a fluid include: 1) measuring the weight of fluid in a flask of fixed volume; and 2) employing the buoyancy of a density float for the assessment of fluid density. Both of these methods require collection of large samples from a fluid-processing device such as a pipeline or reactor for off-line measurements. For a given solution, density relates to the solute concentration of the solution. Although the density measurement is not specific to what solute is in the solution, these two density measurement methodologies and others to be described later have been used as a means to assess solute concentration.

A mechanical device based on resonance has been available to measure density of a fluid sample or that of a flowing fluid on-line. The device has a hollow U-tube with its two ends fixed on a heavy base. The fluid can be infused to fill the U-tube or made to flow along the tube. By measuring the frequency that the U-tube resonates, one then determines the mass of fluid in the U-tube. Since its volume is fixed, the mass is converted to the fluid density. This mechanical density measuring system (MDMS) has high sensitivity and reproducibility in the dynamic measurement of fluid density.

As a fourth density measurement method, one measures the sound velocity of fluid for the determination of the compressibility and density of fluid. Krivitski, in U.S. Pat. Nos. 5,453,576 and 5,685,989 describes an apparatus and method for measuring several hemodynamic parameters by using a sound velocity sensor. The ultrasound transducer is excited to emit a pulse of ultrasound. After its passage through a fluid medium such as the blood, a receiving transducer senses the ultrasound pulse. A protocol to compare the excitation and receiving ultrasound signals determines the transmission time through the blood and subsequently its sound velocity. The information contained in the '576 and the '989 patent is incorporated by reference as though cited in its entirety. When their device is used to measure blood density change for the computation of blood volume, a linear approximation of a non-linear relationship is employed to convert the sound velocity to the density of the blood. Furthermore, the device of the '576 patent has limited sensitivity so as to require the imposition of a large change in blood density for accurate assessment of blood volume.

The system patented by Schneditz in U.S. Pat. No. 5,830,365 also utilizes sound velocity for the measurement of transmission time delay through the blood and then its total protein concentration. A clinical protocol to change the ultrafiltration rate as a patient undergoing hemodialysis treatment is described to produce the change in density, which is assessed through a sound velocity monitor. An equation is deduced to compute from the change measurement the blood volume circulating in the patient. The monitor to measure density is about one order of magnitude less sensitive than that provided by the MDMS or our density/solute monitor. As a result, the application of Schneditz's method to measure blood volume is limited to cases that the change in sound velocity being imposed through the clinical protocol is large.

The fifth density measurement method employs the attenuation due to the absorption of radioactivity by the fluid as a means to assess its density. Approval by regulatory agency is required for this method.

SUMMARY OF THE INVENTION

The present invention is directed to a density/solute monitor including an ultrasound probe and a signal processing unit for accurately and reliably determining the phase shift of ultrasound transmission through a fluid and then the sound velocity of the fluid and a method of applying the same to biological or chemical processing systems. A set of equations and measurements by other modalities are incorporated to deduce from the sound velocity the compressibility, density, concentration of specific solute, and concentration of particulate matters of the fluid. The monitor can be used to determine the mass flow of solute, to improve the performance of chemical processes, and to optimize process design. The improvement and optimization can lead to more efficient collection of solutes, more solute purity in the collection, and better efficiency of the chemical processes.

The novel embodiments of the density/solute monitoring system include a signal processing unit with simple hardware and software to determine at high accuracy phase shift and transmission time of ultrasound signals; a two-fluid calibration procedure to convert the phase shift and transmission time in terms of sound velocity; an appropriate placement of the probe to time the passage of certain solute injected upstream of the probe; the use of two probes in series to measure volume flow; a procedure to work with the MDMS for the establishment of an empirical relation between the density and sound velocity of fluid and to account for the dependence on temperature; the calculation of the compressibility of the fluid to derive its relation with the sound velocity and density of the fluid; a set of computer files and equations specific to given solute, solution and density/solute monitor on the conversion of density to the solute concentration in the solution.

The ultrasound probe can work alone or in combination with other detection modalities to achieve more functionality for the density/solute monitor. Other detection modalities include:

(1) The use of optical absorbance and/or reflectance of light at frequency ranging from infrared to ultraviolet, impedance and conductivity of microwave, and absorbance of radiation for better identification of the solute of interest;

(2) A procedure using the injection of certain solution and the sensitivity of the ultrasound probe to calibrate and determine the sensitivity of other detection modalities;

(3) A procedure to detect the movement of tracers for system characterization.

The use of these embodiments will enable one to achieve at least one of the following features:

(1) A multi-functional detection system of low cost;
(2) Accurate assessments on the flow and passage of specific solute;
(3) Efficiency in the collection and purification of specific solute with the technology of chromatography;
(4) Crucial information for industrial engineers to optimize the process design;
(5) Information for diagnosis and prevention of cardiac deficiencies in patients.

By making use of the high sensitivity of the ultrasound probe, the multi-modality monitor gains additional power to determine the concentration of specific solute in the solution, the passage of specific solute through a chromatography column, and the dynamic changes of the solute in chemical or biological processing systems. In applying these probes and methods to paper, petroleum, chemical, pharmaceutical, food and bioprocessing industry; the engineers can determine more accurately the mass flow being transported through pipeline, achieve better solute purity in solution collected from chromatography column, and control more responsively the chemical or biological processing. The multi-modality methodology is applicable to human for determinations of blood parameters, vascular functions, and cardiac performance. The information provides key measurements for physicians to maintain homeostasis of the patient and to diagnose or to prevent cardiac deficiencies such as hypotension and shock in patients undergoing hemodialysis treatment or subject to trauma or burns.

Multi-modality probes and methods are described:

1. To monitor the phase shift between the emitting and receiving ultrasound and the time of sound transmission in the fluid in pipelines or reactors;
2. To use a set of relationships and procedures to convert these phase and time measurements into accurate assessment of sound velocity, density, compressibility, solute concentration, and their changes;
3. To monitor a number of fluid properties in optical absorbance, reflectance, conductivity, impedance, magnetic resonance, radioactivity attenuation, and tracers to better specify the solute being assessed and to better time the flow and passage of the solute;
4. To employ these assessments for more efficient operation and control of chemical, physical and biological process common to chemical, pharmaceutical, food product, paper, and petroleum industries;
5. To improve the probes and algorithm for use as blood volume monitor claimed in U.S. Pat. Nos. 6,740,036 and 6,485,427 B1.

DESCRIPTION OF THE PREFERRED EMBODIMENTS

Figure 1:
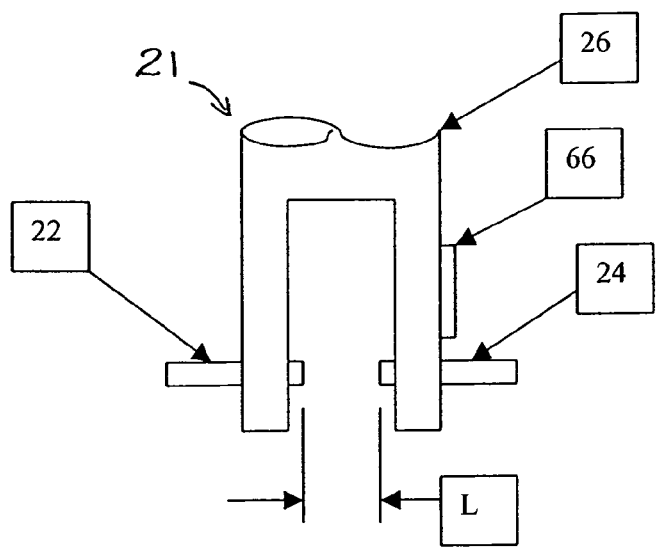
FIG. 1 is a schematic drawing of an embodiment of the ultrasound probe in the insertion mode. It has a pair of ultrasound transducers and a thermistor. The probe is inserted into a pipeline or reactor for measurements of fluid inside. In this design, the transducers and thermistor are in direct contact with the fluid.

FIG. 1 shows an embodiment of the ultrasound probe in the insertion mode. In this embodiment, the probe 21 includes an inserting mechanism 26, which is mounted with the ultrasound emitting transducer 22, the receiving transducer 24, and the thermistor 66. With the insertion of the probe into a fluid system such as a chemical system or pipeline, the surfaces of the transducers 22 and 24 and thermistor 66 are directly in contact with the fluid flowing there.

Figure 5:
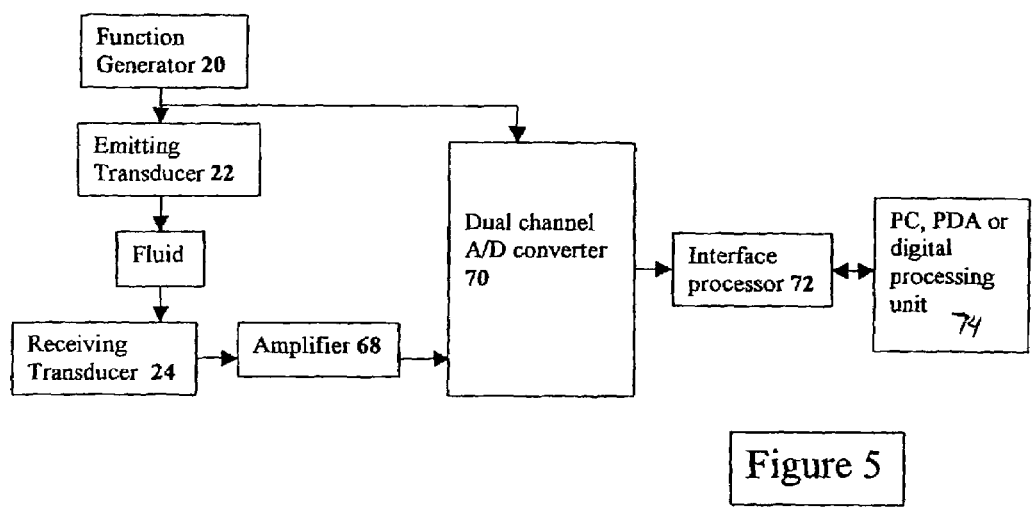
FIG. 5 depicts the hardware employed to digitize the excitation signal (or the signal to the emitting transducer) and the signal from the receiving transducer, the storage of the data in the memory of interface processor, and then its transfer to the computer for the determination of the phase shift.
Figure 6:
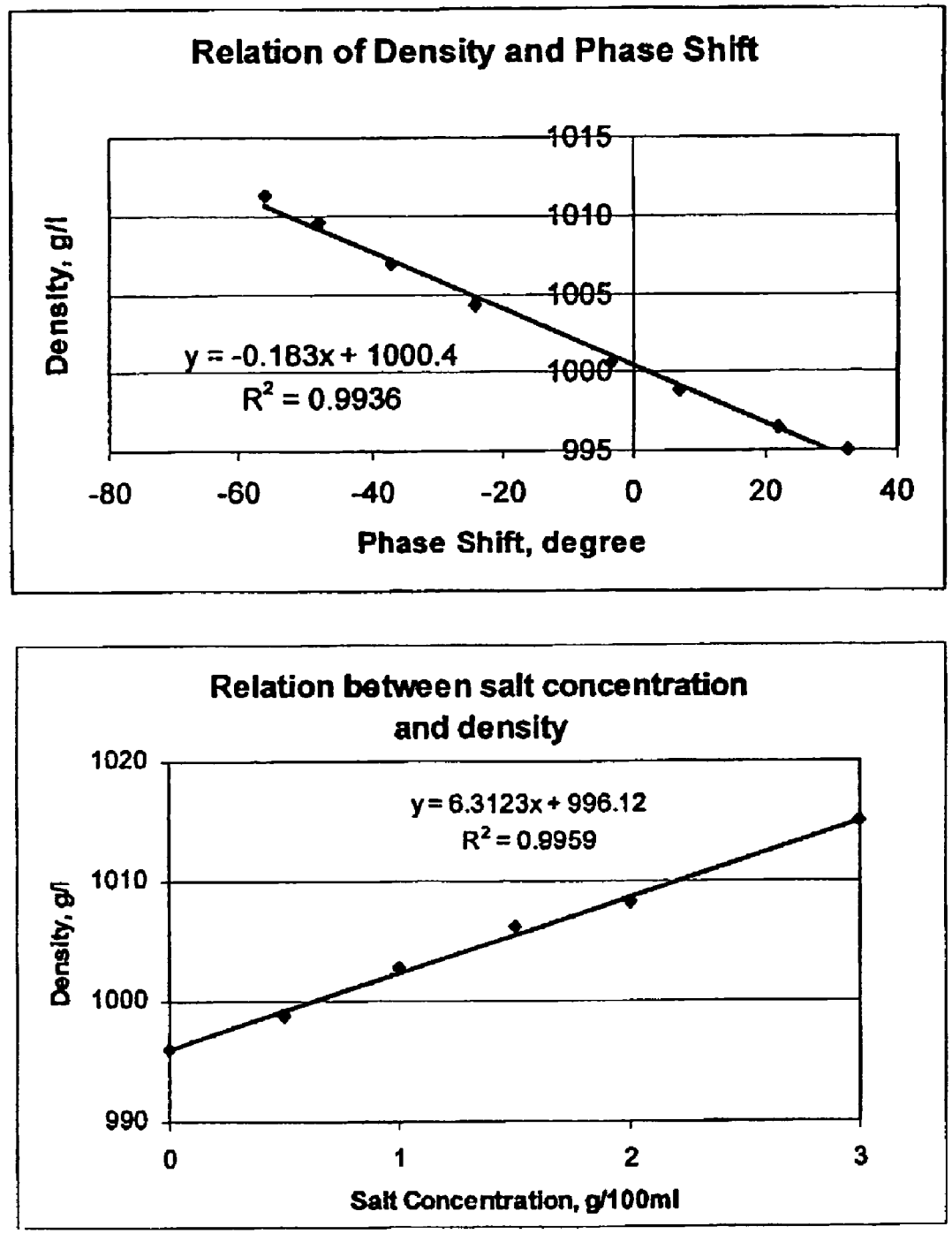
FIG. 6 is the density of saline, phase shift, and salt concentration in saline at 23° C. The density is measured by a MDMS and the phase shift by an insertion ultrasound probe. No gating of the excitation signal was employed for this data set. The range of density is achieved by varying the salt concentration in the saline.

Transducers 22 and 24 are part of said ultrasound probe, which is attached to a signal processing unit. The signal processing unit is comprised of a function generator 20, an amplifier 68, a dual channel analog-to-digital (A/D) converter 70, an interface processor 72, and a computing mechanism 74 as shown in FIG. 5. The function generator 20 transmits a power signal, preferably via a cable, to activate the emitting transducer 22 into producing a train of ultrasound wave at an appropriate frequency ($f_{ultrasound}$). One preferred frequency is about 5 Megahertz, but any frequency deemed appropriate by one skilled in the art would suffice.

This power signal is also digitized as an excitation signal by one channel of the dual channel (A/D) converter 70 within the ultrasound signal-processing unit. When the excitation frequency of the excitation signal is chosen as 5 Megahertz, the emitting transducer emits ultrasound at the frequency of 5 Megahertz. The sampling frequency of the A/D converter is chosen to be an integer multiple of the excitation frequency. This integer is designated as m. For an ultrasound/excitation frequency of 5 Megahertz and an A/D converter's sampling frequency ($f_{sampling}$) of 65 mega samples per second (MSPS), m is 13, meaning there are 13 digitized samples over one full ultrasound oscillation. Or, if an A/D converter with a sampling frequency of 105 MSPS is used, m will be 21. When low cost A/D converters at higher sampling frequencies become available, the ultrasound frequency or the number of samples per oscillation cycle can be increased to improve the resolution of the density/solute monitor. The receiving transducer 24 receives the ultrasound wave after its passage through the fluid. The signal is amplified by amplifier 68 and digitized through the other channel of the dual channel A/D converter 70. Both the digitized excitation and receiving signals are sent to the interface processor 72 for storage and a computing system 74 for analysis.

Figure 4:
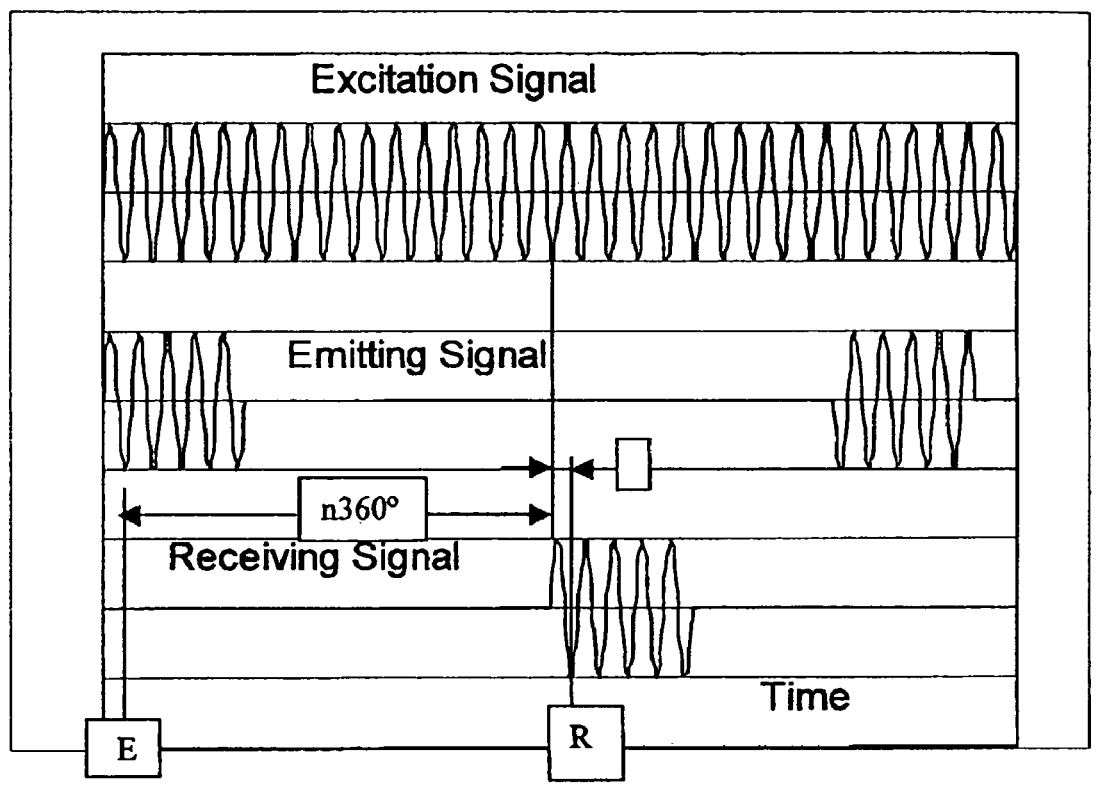
FIG. 4 is an illustration identifying the phase and time shift among the excitation signal, that to the emitting ultrasound transducer, and that from the receiving ultrasound transducer. The excitation depicted has a constant frequency. Only over a finite time (five oscillation periods are depicted here and then repeated 26 cycles later), the excitation signal is passed through to excite the emitting transducer to emit ultrasound. After the transmission of ultrasound through the fluid, the receiving transducer picks up the ultrasound. Its amplified version is depicted here. The transmission time, exemplified by the time for valley E in the emitting signal to be transmitted to valley R in the receiving signal, is composed of n oscillation periods (an n of is depicted) and a phase shift between the excitation signal and receiving signal ($\phi$).

The system of the present invention uses continuous measurements of phase shift and transmission time of ultrasound waves in a fluid to assess sound velocity, density, solute concentration, compressibility, and changes in these quantities. Once the ultrasound probe is inserted into a fluid and the signal processing unit described above transmits and digitizes ultrasound waves through the fluid, the computing system 74 is ready to determine phase shift and transmission time. The transmission time ($T_{shift}$) depicted in FIG. 4 is the time for valley E of the emitting signal after transmission in becoming valley R of the receiving signal. With the use of continuous wave, the period of each oscillation ($T_0$) is $1/f_{ultrasound}$. To facilitate the determination of transmission time, it is divided into two parts. The first part is composed of n periods of oscillation, which is the time for valley E to reach a valley of the excitation signal that is closest to the valley R. A peak detector and a clock determine this shift. The second part reflects the phase shift from the valley of the excitation signal to the valley R. To be determined from the procedure described next, this phase shift $\phi$ has the range in between $-180°$ and $180°$. Accordingly the transmission time is expressed as:

$$T_{shift} = T_0(n + f/360°) \quad \text{Equation 1}$$

$$\text{or} \quad = (n + f/360°)/f_{ultrasound} \quad \text{Equation 2}$$

or

Let us identify the excitation and receiving samples stored on the interface processor as $E_i$ and $R_i$ respectively with i being the sampling index. Once some 1000 to 2000 samples from each signal are stored, the computer instructs the interface processor to transfer the data for processing. First, their average is determined and subtracted to achieve a zero average. Then the data are multiplied and summed as specified by Equation 3 and 4.

$$M_1 = \Sigma(E_i R_i) \text{ with the summation from } i=1 \text{ to } N \quad \text{Equation 3}$$

$$M_2 = \Sigma(E_i R_{i+j}) \text{ with the same summation as above} \quad \text{Equation 4}$$

where j is chosen so that the receiving signal is shifted by about one quarter of a cycle. It is $$j = \text{Round}(m/4) \quad \text{Equation 5}$$

The function Round stands for the nearest round off of a number to an integer. The total number N used for the summation is chosen to be an integer multiple of m and to cover most of the period over which we have values for the receiving signal. When the number of cycles to be covered is larger than 60, our computation results indicate good sensitivity in sound velocity determination will be achieved. With $M_1$ and $M_2$ so calculated, we determine the phase shift of the receiving signal from the emitting signal ($\phi$) as:

$$\phi = \tan^{-1}[M_2/(M_1 \sin \theta) - \cot \theta] \quad \text{Equation 6}$$

where $\phi$ and $\theta$ are expressed in the unit of degree and $\theta$ is $360° \cdot (j \cdot f_{ultrasound}/f_{sampling})$. If m is a multiple integer of 4, then $\theta=90°$ and Equation 6 reduces to the one commonly used in phase lock computation:

$$\phi = \tan^{-1}[M_2/M_1] \quad \text{Equation 7}$$

Two fluids typical to certain fluid processing will be used to calibrate the probe in the factory or in situ. Let the sound velocity of the two calibrating fluids be $c_1$ and $c_2$ and the corresponding phase shift be $\phi_1$ and $\phi_2$. The time for the ultrasound to transmit from the emitting transducer through the fluid to the receiving transducer relates the measured phase shift by these equations:

$$(n+\phi_1/360°)T_0 = L/c_1 \quad \text{Equation 8}$$

$$(n+\phi_2/360°)T_0 = L/c_2 \quad \text{Equation 9}$$

where L is the distance between the transducers for this insertion probe. Suppose the sound velocity of the fluid designated for the measurement is $c_3$ and the measured phase shift is $\phi_3$. Then they are related by $$(n+\phi_3/360°)T_0 = L/c_3 \quad \text{Equation 10}$$

Equations 8, 9 and 10 can be reorganized to yield Equation 11 to determine $c_3$ from $\phi_3$:

$$c_1/c_3 = 1-(1-c_1/c_2)(\phi_3-\phi_1)/(\phi_2-\phi_1) \quad \text{Equation 11}$$

Using a series of fluid samples having a range of solute concentration, we can use the ultrasound probe and the MDMS to determine the sound velocity (c) and the density ($\rho$) respectively. It is known that the compressibility ($\kappa$) of the fluid relates to sound velocity and density by $$\kappa = \rho/c^2 \quad \text{Equation 12}$$

By plotting the measurements and calculations against each other, we obtain a set of empirical equations for converting the measured sound velocity in terms of density, compressibility, or solute concentration.

For most cases in industrial and clinical application, the difference among the three sound velocities is smaller than a few percentages. Thus, we can linearize Equation 11 to relate the sound velocity to phase shift by:

$$c_3 = c_1 + (c_2-c_1)(\phi_3-\phi_1)/(\phi_2-\phi_1) \quad \text{Equation 13}$$

Since the change of density is also smaller than a few percentages, the change in density and that in sound velocity can be related through a linear equation. Accordingly, Equation 13 can be converted to the following form for the determination of density:

$$\rho_3 = \rho_1 + (\rho_2-\rho_1)(\phi_3-\phi_1)/(\phi_2-\phi_1) \quad \text{Equation 14}$$

where $\rho_3$ is the density being measured, and $\rho_1$ and $\rho_2$ the density of the calibrating fluids. In the case of protein solution, the density is linearly related to the concentration of protein C. If the fluid in the pipeline or chemical reactor also has its solute concentration linearly related to the density, we have Equation 15 to derive from the phase shift measurements the solute concentration $C_3$:

$$C_3=C_1+(C_2-C_1)(\phi_3-\phi_1)/(\phi_2-\phi_1) \quad \text{Equation 15}$$

In the special case that the solute concentration for one calibrating fluid $C_1$ is zero, Equation 15 is simplified to:

$$C_3=C_2(\phi_3-\phi_1)/(\phi_2-\phi_1) \quad \text{Equation 16}$$

Equation 13 is regarded as a two-constant calibration equation of the probe or probes of the monitoring system to convert phase $\phi_3$ to $c_3$. In this equation, $c_1$ is given and the two constants are $\phi_1$ and $(c_2-c_1)/(\phi_2-\phi_1)$. These two constants are determined by the two fluid calibration procedure. In the same way, one can define the two constants in equation 14 or 15 for converting phase to density or solute concentration respectively.

A signal processing procedure similar to the probe calibration discussed above is applicable to the case where the emitting ultrasound is identical to the excitation signal, i.e. without the gating shown in FIG. 4. In this scheme, wave reflection will take place and the total transmission time cannot be determined. However, Equations 3, 4 and 6 can be used to determine the phase shift of the receiving ultrasound from the emitting one. With the values of $\phi_1$ and $\phi_2$ determined for a given ultrasound probe in the factory, one finally uses Equation 14 to 16 to determine from the phase shift measurement 93 the sound velocity, density, and solute concentration. This computation scheme as applied to blood, saline and plasma has been described in U.S. Pat. No. 6,740,036, to which the present application claims priority. The computation scheme and monitoring system can be used to determine sound velocity, density, and solute concentration measurements for various fluids in industries including, but not limited to, the following: paper, petroleum, chemical, pharmaceutical, food, and bioprocessing industries.

Figure 3:
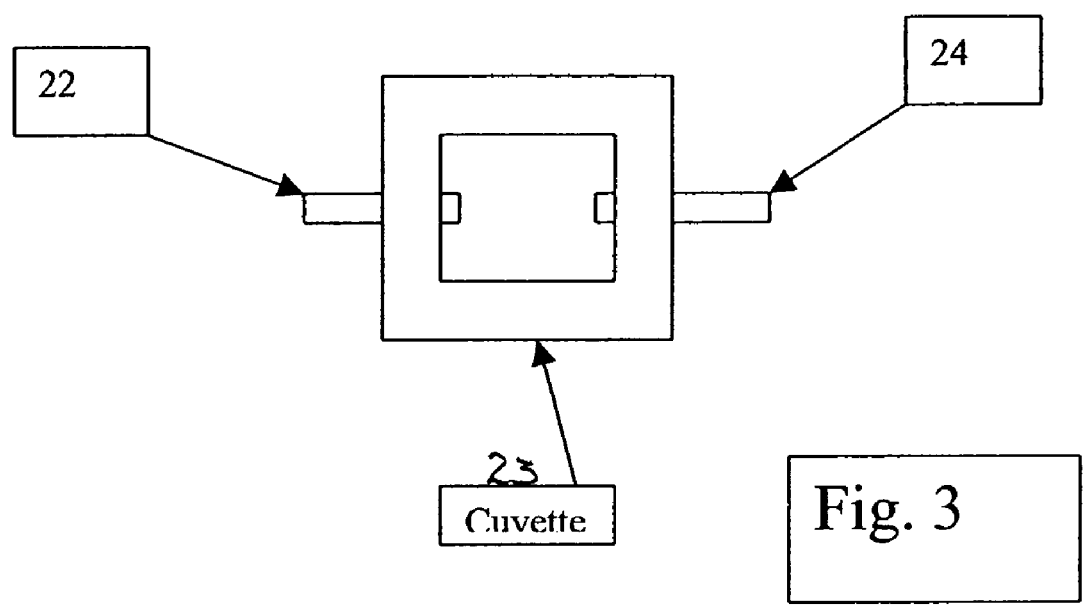
FIG. 3 is a schematic drawing of an embodiment of the ultrasound probe in the cuvette mode. Pair of ultrasound transducers and a thermistor are mounted on the sides of the cuvette for which it contains the fluid for measurement. In this design, the transducers and thermistor are in direct contact with the solution. The housing containing the cuvette has the function of maintaining temperature at a preset value.

The equations derived for the insertion probe are applicable to the cuvette mode of the ultrasound solute probe as shown in FIG. 3. The transducers are identified as 22 and 24. In this case the cuvette 23 is housed in a controlled environment with a preset temperature.

Figure 2:
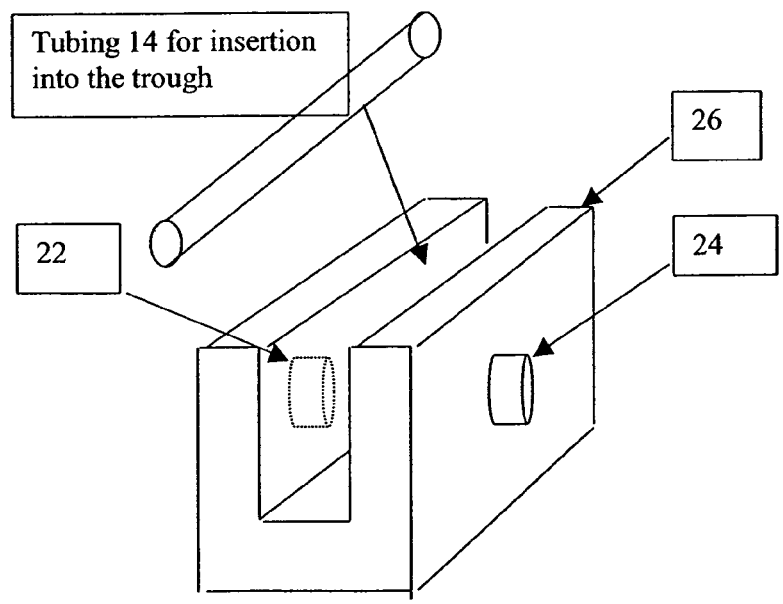
FIG. 2 is a schematic drawing of an embodiment of the ultrasound probe in the clip-on mode. It has a pair of ultrasound transducers and a thermistor. The probe is clipped on to a tube or column with flowing solution. In this design, the transducers and thermistor have no direct contact with the solution.

The clip-on mode of the ultrasound probe depicted in FIG. 2 has a trough for the insertion of tubing 14. In this configuration, the transmission time from transducer 22 to transducer 24 includes the transmission time through the walls of the tube. However, the subtraction process employed in the derivation of Equation 11 also has the additional transmission time subtracted out so that Equation 11 remains valid for the probe of clip-on mode. In this embodiment, the clip 26 has a trough about 5 mm for the insertion of hemodialysis tubing 14 whose outside diameter is about 6.2 mm. Ultrasound gel is used to facilitate the insertion of the tubing 14 into the clip and to provide an airtight contact between the tubing 14 and the transducers 22, 24, preventing problems and errors that can be caused by the reflection of ultrasound through air bubbles likely trapped between the transducers and tubing.

Pipeline, tubing, or chromatography columns with a diameter other than 6.2 mm can also be used in the system and the dimensioning adjustments to the clip will be obvious to those skilled in the art. The resulting adjustment to convert phase shift to density or solute concentration will be incorporated through the parameters stored in a data file accompanying the probe. To gain a larger receiving signal, one can employ a lower ultrasound frequency such as 1 Megahertz to power the emitting transducer. With the sampling frequency remaining at 65 MSPS, one will have 65 samples digitized over one period of oscillation while the total number of samples used in the determination of phase shift may remain in the range of 1000 to 2000.

When the insertion or clip-on mode of the solute monitor is mounted onto the end of a column of chromatography process to assess solute concentration, we note that the transmission time includes that through the column wall, the porous beads in the column and the fluid. The presence of the beads will alter the relation between the fluid density and phase shift, which can be resolved by the on-line calibration procedure described later.

In application, the ultrasound probe of insertion mode is inserted into a fluid processing system such as a pipeline or chemical processing system for continuous measurement of the phase shift of ultrasound transmission in the fluid. In addition, a test fluid with a density $\rho_{test}$ at a volume $\Delta V$ is injected into the system upstream of the probe. Let the flow be Q and the volume of fluid situated between the injection and measurement site be $V_1$. According to the density dilution theory, one deduces from the principle of mass conservation the relation specified in Equation 17

$$Q\int(\rho_0-\rho)]dt=\Delta V(\rho_0-\rho_{test}) \quad \text{Equation 17}$$

where $\rho$ is the density being measured, $\rho_0$ the steady state density before the injection, and the integration limit is over the time that the density is transiently deviated from the steady state density. Corrections can be made for the integration when the injected fluid re-circulates back through the probe. With most small injections, the density change from $\rho_0$ is small.

Equation 14 can be re-expressed as a linear relation between density change $\Delta\rho$ and the phase change $\Delta\phi$ with a calibration constant $b_1$, i.e.

$$\Delta\rho=b_1\Delta\phi \quad \text{Equation 18}$$

Its substitution into Eq. 17 yields Equation 19 for in situ, on-line determination of the calibration constant $$b_1=(\Delta V/Q)(\rho_{test}-\rho_0)/\int\Delta\phi dt \quad \text{Equation 19}$$

Using Equation 14, one can convert Equation 17 to Equation 20:

$$Q=\Delta V(\phi_{test}-\phi_0)/\{\int(\phi-\phi_0)dt\} \quad \text{Equation 20}$$

where $\rho_0$, $\rho_{test}$, $\rho$, $\phi_0$, $\phi_{test}$ and $\phi$ are respectively the replacements of $\rho_1$, $\rho_2$, $\rho_3$, $\phi_1$, $\phi_2$ and $\phi_3$ in Equation 14. Equation 20 can therefore be used for the calculation of the flow The consideration on mean transit time, volume and flow in the density dilution theory yields Equation 21 to relate the volume and flow:

$$Q=V_1\int(\phi-\phi_0)dt/\{\int(\phi-\phi_0)tdt\} \quad \text{Equation 21}$$

From Equation 20 and 21, we can solve for the value of $\phi_{test}$ when the flow and volumes are known. The difference between the solute concentration in the flowing fluid and that in the test fluid can now be related to the difference between $\phi_{test}$ and $\phi_0$.

As another alternative to measure the flow, one can place two probes in two locations along the pipeline or chemical processing system. The flow can be calculated as:

$$Q=V_{4\text{-}5}\int(\phi_4-\phi_0)dt\}/\{\int(\phi_5-\phi_4)tdt\} \quad \text{Equation 22}$$

where $V_{4\text{-}5}$ is the fluid volume of the pipeline or chemical system in between the two probes, $\phi_4$ is the phase shift measured by the upstream probe, and $\phi_5$ that by the downstream probe.

There are several working models of the ultrasound system to assess blood density. In one signal processing embodiment the transducer 22 of FIGS. 1 and 5 is activated by any commercially available pulser/receiver, including a Panametrics 5072PR pulser/receiver, to emit ultrasound impulses of about 15 to 20 Megahertz at a rate of about 100 Hertz. Each pulse contains about 4 to 6 oscillations. After its transmission through the flowing blood, the second transducer 18 receives the ultrasound pulse. The trigger signal from the pulser/receiver triggers a digital oscilloscope such as a LeCroy 9350AL oscilloscope or a Synatec A/D converter to sample the signal from the receiver 24 at 100 Megahertz to 1 Gigahertz. Some ten digitized samples of the pulse are compared by a computer for the determination of the phase shift. The sensitivity achievable with this process appears at best of the order nanosecond.

In another embodiment, the signals from the receiving transducer and the function generator, which excites the emitting transducer, are processed by a phase lock amplifier such as Stanford Research System SR 844, which is powerful in processing signals with a frequency as high as 200 Megahertz. Many digitized samples from the continuous ultrasound are employed for the calculation. At the ultrasound frequency of interest here, the use of SR 844 provides sensitivity about one order of magnitude higher than the pulse system described previously.

In our preferred embodiment, the ultrasound probe is used in conjunction with a novel ultrasound signal processing unit, a new computation scheme, and a two-fluid calibration procedure. This new scheme is an improved version of the system described in U.S. Pat. No. 6,740,036 as we relax the requirement that the value of m in Equation 5 must be an integer multiple of 4. In the current invention, the digitized data of some 100 oscillations (or 1000 to 2000 digitized samples) are employed. In comparison with the pulse procedure, the use of more samplings for signal processing enables us to gain higher sensitivity in phase shift determination.

As in the SR 844 phase lock amplifier, the 90-degree shift of the excitation or receiving signal in Equation 4 is accomplished by electronic means. Our scheme achieves the shift by shifting the index of digitized receiving signals for multiplications and summations. Since the shift in general may not be exactly 90-degree, the more general Equation 7 is deduced to carry out the computation of the phase shift between the emitting and receiving signal. Our test results indicate that our signal processing unit and the use of Equation 3, 4 and 6, even with a sampling rate of 65 MSPS (or about 15 ns a sample), can achieve a phase resolution of the order 0.03 ns, which is comparable to that via the SR844 amplifier. Only with this sensitivity, can the density and solute concentration expected to occur in industrial and clinical applications be measured.

Because of the new algorithm and the simplicity in hardware design, our invention is in the position of being built as an IC chip. The end result of the use of IC chip will be a monitor with a much lower manufacturing cost than a system using SR 844 phase lock amplifier to process the signals.

The solutes in the solution may exhibit different characteristics to absorbance or reflectance at various wavelength of the light. In a preferred embodiment, the ultrasound probe of the monitoring system works in conjunction with a light-emitting mechanism such an optical detector or a spectrophotometer to measure the absorbance and/or reflectance of fluid in the monitoring system. An optical detector preferably comprises at least one light source and filter and at least two photomultipliers. The spectrophotometer preferably comprises at least one light emitting diode and at least two photodiodes. Conventionally, optical modality requires the detector be calibrated with solutions of different solute concentration. However, as described later, one can employ the ultrasound probe and the on-line procedure to calibrate the optical modality. Let us illustrate this procedure with blood as the fluid and the optical modality being an IR detector. At an appropriate IR frequency, the detector has been used to assess hematocrit, the volumetric percentage of red blood cells in blood.

In clinical practice, the monitors are mounted onto the hemodialysis circuit, which withdraws blood from an artery and returns the blood after its passage of the hemodialysis machine back to a vein of the patient. A bolus of isotonic saline is injected into the circuit to flow through the hemodialysis machine and then the monitors. The sound velocity of saline is lower than that of blood. The passage of the saline after its mixing with the circulating blood will be recognized by the density monitor as a reduction in phase shift. Since there are no red blood cells in saline, we also expect to see a transient decrease in hematocrit, which will be picked up by the IR detector because of the resulting change in absorbance or reflectance characteristics of blood. Let us express the measurement of the optical detector as optical density (OD). When the blood is mixed with a saline of density $\rho_s$ and no red blood cells, the dilution of the density $(\rho_b)$ and hematocrit (H) of blood follow Equation 21.

$$(\rho_b - \rho_s) = [(\rho_{b,1} - \rho_s)/H_1]H \qquad \text{Equation 21}$$

where $\rho_{b,1}$ is the steady-state blood density and $H_1$ is the steady-state hematocrit before the saline injection.

By plotting the change in optical density $\Delta OD$ against that of density $\Delta \rho_b$ as detected through the ultrasound probe, we can obtain the slope $b_2$ in the linear relation of Equation 22:

$$\Delta \rho_b = b_2 \Delta OD \qquad \text{Equation 22}$$

Its combination with Equation 21 for saline dilution yields Equation 23:

$$\Delta H/H_1 = [b_2/(\rho_{b,1} - \rho_s)] \Delta OD \qquad \text{Equation 23}$$

In practice, the optical detector is located, for example, downstream of the ultrasound probe. To carry out the data analysis through Equation 22, we will adjust the optical signal by a time for which the linear fit between the optical density and density has the correlation coefficient closest to unity. Then the slope of this linear fit is taken as $b_2$. Once the slope is measured with this on-line procedure, Equation 23 is the calibration equation to convert the change in optical density to the hematocrit ratio $(\Delta H/H_1)$.

In industrial applications, the injectate may contain a number of solutes of interest to the chemical and biological process. Each solute may have different absorbance or reflectance characteristics. Thus the spectrum of the optical detector will be set up to differentiate the absorbance or reflectance of the solutes. Because of difference in molecular sizes or activities, the passage of these solutes through the chemical system, biological reactor or chromatography column may occur at various times. Their presence in the flowing fluid will alter the phase shift and light absorbance as the fluid passing through the monitor. A procedure similar to hematocrit calibration can be applied as an on-line means to calibrate the optical detector in industrial setting. Conversely, the specificity of the optical detector in solute identification allows us to pinpoint which passage detected by the ultrasound probe is associated with which specific solute.

The passage of solute as detected by the ultrasound probe can now be used to activate a fractional collector to collect the solution containing most of the specific solute. This on-line control will reduce the collection of other solutes coming through the probe at other times and to improve the purity of the specific solute in the collection. This characteristic to identify the presence of solutes through the use of density/solute monitor can also be used to improve the collection of solution containing no solutes for reuse by the chromatography process.

γray is absorbed by the fluid over its passage. The attenuation of γ ray, a physical characteristic of the fluid, can be associated with and thus be used to determine the density of the fluid. The combination of this attenuation with the ultrasound characteristics may further enhance our ability to differentiate the kind of fluid flowing pass the density/solute monitor.

Infusion of hypertonic saline has been used clinically to extract fluid from the tissue in human body to the circulation. The extracted fluid has a density lower than the blood. Thus its mixing with blood will lower the density of blood. Consequently, multi-modality monitor on conductivity and phase shift may allow us to assess the process of fluid extraction from the tissue.

Tracers have been used to monitor dynamic events occurring in a chemical system, pipeline, or the human circulation system. Some tracers can be detected by magnetic resonance imaging (MRI) system or CT scan. If the tracers are in the form of vesicles containing a fluid or other medium that its density is different from that of the flowing fluid, then the density or compressibility of fluid may be altered by the presence of tracers and be detected by the density monitor. The tracer can be a substance tagged with radioactive element or dye. Radioactivity counter can detect the former and optical detector set at the frequency most sensitive to the dye can detect the latter. The use of multi-modality detection systems and tracers may further improve the sensitivity and specificity of the density/solute monitor to better track the movement of solutes through chemical processing system or human circulation.

What is claimed is:

1. A system for monitoring fluid in a fluid processing system comprising:
   at least one ultrasound probe comprised of an emitting transducer and a receiving transducer;
   a signal processing unit attached to said at least one ultrasound probe, said unit comprised of at least a function generator, a dual channel analog-to-digital converter, and an interface processor;
   a computing system adjacent to said signal processing unit, said computing system receiving digitized signal information from said signal processing unit; and
   a thermistor attached to said signal processing unit to measure the temperature of said fluid;
   wherein, said function generator generates a power signal to activate said emitting transducer to emit an ultrasound wave of specific frequency over a specific time period repeatedly through said fluid to be received as a receiving signal by said receiving transducer;
   wherein, said analog-to-digital converter digitizes said power signal as an excitation signal at a specific sampling frequency;
   wherein, said analog-to-digital converter digitizes said receiving signal received by said receiving transducer at a specific sampling frequency;
   wherein, said computing system computes transmission time and phase shift between said excitation and receiving signals; and
   wherein, said computing system uses said phase shift measurement to compute sound velocity, density, compressibility, and solute concentration measurements of the fluid at a measured temperature.

2. The system of claim 1, wherein said fluid processing system is a chemical processing system.

3. The system of claim 2, wherein said fluid is a chemical solution.

4. The system of claim 2, wherein said fluid is oil.

5. The system of claim 2, wherein said fluid is paper slurry.

6. The system of claim 1, wherein said fluid processing system is a biological fluid processing system.

7. The system of claim 6, wherein said fluid is blood.

8. The system of claim 6, wherein said fluid is a food product.

9. The system of claim 1, wherein said at least one ultrasound probe is calibrated using an in-factory calibration procedure using at least two test fluids to assess two constants for converting phase shift measurement to sound velocity, density, or solute concentration.

10. The fluid monitoring system of claim 1, wherein said at least one ultrasound probe is calibrated using an on-line calibration procedure using at least one test fluid injected into said fluid processing system at a site upstream of said at least one ultrasound probe.

11. The system of claim 10, wherein injection of said at least one test fluid into said fluid processing system facilitates quantification of specific solutes in said test fluid by said signal processing unit.

12. The system of claim 10, wherein said at least one ultrasound probe is two probes, said two probes placed in series to measure changes in density due to the passage of said at least one test fluid.

13. The system of claim 1, further comprised of an amplifier, said amplifier amplifying said receiving signal from said receiving transducer and directing said receiving signal to said analog-to-digital converter.

14. The system of claim 1, wherein said signal processing unit is built into an IC chip.

15. The system of claim 1, wherein both said emitting signal and said excitation signal are continuous waves.

16. The system of claim 1, further comprised of a light-emitting mechanism, wherein said mechanism induces and measures absorbance and/or reflectance of light in said fluid.

17. The system of claim 16, wherein said light-emitting mechanism is an optical detector, said optical detector comprised of at least one light-emitting diode and at least two photodiodes.

18. The system of claim 16, wherein said light-emitting mechanism is a spectrophotometer, said spectrophotometer comprised of at least one light source, at least one filter, and at least two photomultipliers.

19. The system of claim 16, wherein said computing mechanism uses said density measurement and said absorbance and/or reflectance measurement to monitor passage of a specific solute through said fluid processing system.

20. The system of claim 1, further comprising a conductivity/impedance monitoring device, said device comprised of a pair of electrodes and electronics, wherein said at least one ultrasound probe works in conjunction with said conductivity/impedance monitoring device to assess conductivity and impedance of said fluid of said fluid processing system.

21. The system of claim 20, wherein said computing system uses said density measurement and said conductivity measurement to monitor passage of a specific solute through said fluid processing system.

22. The system of claim 1, further comprised of a radioactivity counter and a radioactivity source.

23. The system of claim 22, wherein said radioactivity counter works in conjunction with said at least one ultrasound probe to assess radioactivity attenuation of fluid.

24. The system of claim 22, wherein said radioactivity counter works in conjunction with an optical detector to measure concentration of dye and radioactive tracer in said fluid.

25. The system of claim 1, wherein said at least one ultrasound probe is a clip-on configuration.

26. The system of claim 25, wherein said at least one ultrasound probe has no contact with flowing fluid and imposes no contamination to said fluid.

27. The system of claim 1, wherein said at least one ultrasound probe is a cuvette configuration.

28. The system of claim 27, wherein said at least one ultrasound probe in cuvette configuration is placed in a temperature-controlled environment.

29. The system of claim 1, wherein said at least one ultrasound probe is mounted at the end of a chromatography column to control collection of specific solutes or a solution containing no solutes.

30. The system of claim 1, wherein said at least one ultrasound probe is an insertion probe.

31. A system for monitoring density and solute concentration of a fluid in a fluid processing system comprising:
at least one ultrasound probe comprised of an emitting transducer and a receiving transducer;
a signal processing unit attached to said at least one ultrasound probe, said unit comprised of at least a function generator, an amplifier, a dual channel analog-to-digital converter, and an interface processor;
a computing system adjacent to said signal processing unit, said computing system receiving digitized signal information from said signal processing unit; and
a thermistor attached to said at least one ultrasound probe to measure the temperature of said fluid;
wherein, said function generator generates a power signal to initiate said emitting transducer to emit ultrasound wave of specific frequency over a specific time period repeatedly through said fluid to be received as a receiving signal by said receiving transducer;
wherein, said analog-to-digital converter digitizes said power signal as an excitation signal at a specific sampling frequency;
wherein, said analog-to-digital converter digitizes said receiving signal, said receiving signal having been received by said receiving transducer at a specific sampling frequency and amplified by the amplifier;
wherein, said computing system computes transmission time and phase shift between said excitation and receiving signals; and
wherein, said computing system uses said phase shift measurement to compute sound velocity, density, compressibility, and solute concentration measurements of the fluid at the measured temperature.

32. A process for monitoring fluid in a fluid processing system, comprising the steps of:
calibrating an ultrasound probe in-factory with at least two in-factory calibrating fluids of known sound velocity to assess phase shift of fluid in terms of sound velocity of said fluid;
calibrating said ultrasound probe on-line with at least one on-line calibrating fluid to assess phase shift of fluid in terms of density of said fluid;
exposing said ultrasound probe into said fluid of said fluid processing system, wherein said ultrasound probe is comprised of an emitting transducer and a receiving transducer and is attached to a signal processing unit comprised of at least a function generator, an amplifier, a dual channel analog-to-digital converter, and an interface processor;
generating a power signal from said generator, wherein said power signal initiates said emitting transducer to repeatedly emit over a specific time period an ultrasound wave of specific frequency through said fluid to be received as a receiving signal by said receiving transducer;
digitizing said power signal as an excitation signal via said analog-to-digital converter;
amplifying said receiving signal via said amplifier;
digitizing said amplified receiving signal via said analog-to-digital converter;
transferring said digitized excitation signal and receiving signal to said interface processor;
transferring said digitized excitation signal and receiving signal data to a computing system, wherein said computing system computes transmission time and phase shift between said excitation and receiving signals, and wherein, said computing system uses said phase shift measurement and said calibrating fluid measurements to compute sound velocity, density, compressibility, and solute concentration measurements of the fluid at a measured temperature.

33. The process of claim 32, wherein said fluid processing system is a biological or chemical reactor.

34. The process of claim 33 wherein said at least one on-line calibrating fluid is a fluid containing tracers or markers used to assess reaction properties of a chemical or biological processing system.

35. The process of claim 32, wherein said fluid processing system is a column of a liquid chromatography system.

36. The process of claim 32, wherein said fluid processing system is a mixing chamber.

37. The process of claim 32, wherein said fluid processing system is a cooking vessel.

38. The process of claim 32, wherein said fluid is blood.

39. The process of claim 38, wherein said computing system determines density, total protein content, hematocrit, plasma density, and plasma protein concentration measurements of said blood.

40. The process of claim 39, wherein changes in blood volume in total circulation and in microcirculation during a clinical treatment is determined using said measurements and said at least one test fluid.

41. The process of claim 39, wherein changes in blood volume and pooling of blood in microcirculation are monitored using said measurements of density and hematocrit of said blood.

42. The process of claim 38 wherein said at least one on-line calibrating fluid is isotonic saline or dialysate.

43. The process of claim 42, further comprised of diluting said fluid of said fluid processing system using a dilution procedure wherein a known volume of said saline or dialysate is infused into said fluid processing system for use in computing blood volume of an animal.

44. The process of claim 32, wherein said fluid is a chemical solution.

45. The process of claim 44 wherein said at least one on-line calibrating fluid is a base solution.

46. The process of claim 32, wherein said fluid is oil.

47. The process of claim 32, wherein said fluid is a paper slurry.

48. The process of claim 32, wherein said calibrating of said ultrasound probe comprises injecting said at least one calibrating fluid into said fluid of said fluid processing system upstream of said ultrasound probe.

49. The process of claim 32, wherein said at least one calibrating fluid is two calibrating fluids.

50. The process of claim 49, wherein said two calibrating fluids have different solute concentrations.

51. The process of claim 32, further comprised of placing at least two ultrasound probes in series to measure changes in density due to passage of a test fluid injected upstream of said ultrasound probes.

52. The process of claim 32, further comprised of monitoring temperature of said fluid of said fluid processing system, wherein said temperature is used by said computing system to convert sound velocity measurements of said fluid to density, compressibility, and solute concentration measurements of said fluid.

53. The process of claim 52, wherein said temperature is monitored using a thermistor attached to said fluid processing system.

54. The process of claim 32, wherein said computing system uses information from said ultrasound probe in conjunction with information from a mechanical density measuring system to convert measurements of sound velocity and phase shift to measurements of density, compressibility, and solute concentration of said fluid.

55. The process of claim 32, wherein said ultrasound probe is exposed to said fluid of said fluid processing system in a temperature-controlled environment.

56. The process of claim 32, further comprised of integrating further detection modality measurements with measurements of said ultrasound probe to monitor passage of a specific solute through said fluid processing system.

57. The process of claim 56, wherein said detection modality measurement is optical absorbance and/or reflectance.

58. The process of claim 57, wherein an optical detector determines optical density from said absorbance and/or reflectance measurement.

59. The process of claim 58, further comprised of on-line calibration of said optical density measurement of said optical detector with said density measurement of said ultrasound probe, wherein said at least one test fluid is injected into said fluid processing system.

60. The process of claim 56, wherein said detection modality measurement is microwave conductivity and/or impedance.

61. The process of claim 56, wherein said detection modality measurement is magnetic resonance.

62. The process of claim 56, wherein said detection modality measurement is radiation attenuation.

63. The process of claim 56, wherein said detection modality measurement is tracers of fluid.

64. The process of claim 56, further comprised of activating of a fractional collector to collect solution containing most of said specific solute.

65. The process of claim 64, wherein said activating collection of a specific solute solution improves purity of a specific solute.

* * * * *